United States Patent [19]

Shields et al.

[11] Patent Number: 5,288,930
[45] Date of Patent: Feb. 22, 1994

[54] PURIFICATION OF 1,1,1,2-TETRAFLUOROETHANE

[75] Inventors: Charles J. Shields, Stockton Heath; Adrian S. Swindells, Warrington, both of England

[73] Assignee: Imperial Chemical Industries PLC, London, England

[21] Appl. No.: 89,611

[22] Filed: Jul. 12, 1993

Related U.S. Application Data

[63] Continuation of Ser. No. 918,681, Jul. 27, 1992, abandoned.

[30] Foreign Application Priority Data

Aug. 2, 1991 [GB] United Kingdom ............... 9116777.5

[51] Int. Cl.⁵ ............................................. C07C 17/38
[52] U.S. Cl. .................................................... 570/179
[58] Field of Search ......................................... 570/179

[56] References Cited

U.S. PATENT DOCUMENTS

| | | | |
|---|---|---|---|
| 4,906,796 | 3/1990 | Yates | 570/179 |
| 5,087,778 | 2/1992 | Yates | 570/179 |
| 5,233,107 | 8/1993 | Jansen | 510/179 |

FOREIGN PATENT DOCUMENTS 0511612 11/1992 European Pat. Off. ............ 570/179

OTHER PUBLICATIONS

Rabo Zeolite Chemistry and Catalysis ACS monograph 171 (1976) p. 34.

Primary Examiner—Alan Siegel
Attorney, Agent, or Firm—Cushman, Darby & Cushman

[57] ABSTRACT

A process for the removal of 1-chloro-2,2-difluoroethylene from 1,1,1,2-tetrafluoroethane by contacting the mixture with a zeolite having a mean pore size in the range of 3.5 Å and 4.8 Å and having potassium as counter cation.

The zeolite having potassium as counter-cation may be produced by cation-exchange with a commercially available zeolite, for example AW-500.

10 Claims, 1 Drawing Sheet

PURIFICATION OF 1,1,1,2-TETRAFLUOROETHANE

This is a continuation of application Ser. No. 07/918,681, filed on Jul. 27, 1992, which was abandoned.

This invention relates to a process for the purification of 1,1,1,2-tetrafluoroethane and in particular to a process for the removal of 1-chloro-2,2-difluoroethylene from 1,1,1,2-tetrafluoroethane.

In recent years chlorofluorocarbons (CFCs), which are used on a large scale around the world, have been perceived as having an adverse effect on the ozone layer and/or as contributing to global warming. CFCs are used, for example, as refrigerants, as foam blowing agents, as cleaning solvents and as propellants for aerosol sprays in which the variety of applications is virtually unlimited. Consequently, attempts have been made to find suitable replacements which will perform satisfactorily in the many applications in which CFCs are used but which will not have the aforementioned damaging effects. The search for suitable replacements has in general centered on fluorocarbons which do not contain chlorine. The hydrofluorocarbon, 1,1,1,2-tetrafluoroethane, also known as HFA 134a, has been of particular interest as one such replacement, in particular as a replacement for dichlorodifluoromethane (CFC 12) in refrigeration applications.

HFA 134a may be produced in a variety of ways, amongst which may be mentioned fluorination of a chlorofluorocarbon or hydrochlorofluorocarbon, for example 1-chloro-2,2,2-trifluoroethane (HCFC 133a), with hydrogen fluoride or an alkali metal fluoride; a catalyst such as chromia, halogenated chromia or chromium oxyhalide may be employed to facilitate the reaction with hydrogen fluoride in the vapour phase.

However, a characteristic of known processes for the production of HFA 134a is that many by-products tend to be produce. Some of the by-products are easy to separate by distillation whilst others are relatively harmless since they are not toxic and their presence does not greatly alter the physical properties of the HFA 134a. However a by-product which is toxic and which thus must be removed or at least reduced in concentration to extremely low levels, for example below 10 ppm, is 1-chloro-2,2-difluoroethylene (HCFC 1122). HCFC-1122 has a boiling point close to that of HFA 134a, and it is thus difficult to separate HCFC 1122 and HFA 134a by distillation.

Processes for the removal of HCFC 1122 from HFA 134a have been described previously. Thus, for example, in U.S. Pat. No. 4,129,603 there is described a process for removing HCFC 1122 from HFA 134a comprising contacting impure HFA 134a with an aqueous solution of a metal permanganate and in U.S. Pat. No. 4,158,675 there is described a process comprising contacting impure HFA 134a with hydrogen fluoride in the presence of a chromium catalyst at 100° C. to 275° C.

It has been proposed to use certain types of molecular sieve for the removal of HCFC 1122 from HFA 134a. Thus, in U.S. Pat. No. 4,906,790 there is disclosed a process for the removal of HCFC 1122 from HFA 134a in which an HFA 134a stream is passed over a molecular sieve which has a pore size of 3.8 to 4.8 Angstroms; the sieve may be carbon or a zeolite such as zeolite 5A or calcium chabazite. However, the use of the zeolites disclosed in the aforementioned U.S. Patent suffers from the disadvantage that the selectivity of the zeolite, that is the amount of HCFC 1122 which is adsorbed by the zeolite as a proportion of the HFA 134a and other halocarbon by-products adsorbed by the zeolite, may be barely satisfactory for practical adoption of the process.

The present invention is intended to remedy this disadvantage and resides in the removal of 1-chloro-2,2-difluoroethylene (HCFC 1122) from 1,1,1,2-tetrafluoroethane (HFA 134a) utilising a zeolite which removes HCFC 1122 from a mixture of HFA 134a, HCFC 1122 and optionally other halocarbons with a greater degree of selectivity than the zeolites proposed hitherto.

According to the present invention there is provided a process for the removal of 1-chloro-2,2-difluoroethylene from 1,1,1,2-tetrafluoroethane which comprises contacting 1,1,1,2-tetrafluoroethane containing 1-chloro-2,2-difluoroethylene with a zeolite having a mean pore size in the range of 3.5 Å and 4.8 Å and having potassium as counter cation.

By the term "mean pore size" there is meant, in the case of zeolites having non-spherical pores, the mean smallest dimension.

The presence of potassium ions ($K^+$) in the structure of the zeolite leads to a substantial improvement in the selectivity of the zeolite for adsorbing HCFC 1122, i.e. the proportion of HCFC 1122 relative to HFA 134a and other halocarbons, for example other hydrofluorocarbons and hydrochlorofluorocarbons, that is adsorbed per unit volume of the zeolite may be increased.

It is believed that this improvement in selectivity may be brought about by the influence of the size of the potassium cation on the effective size and shape of the pores within the zeolite structure. The mean pore size of the zeolite having potassium as counter-cation is preferably between 3.5 Å and 4.5 Å and more preferably between 3.6 Å and 4.2 Å. Changes in electronic interactions and changes in the shape and configuration of the adsorption sites within the zeolite structure are believed also to influence the improved performance of zeolites containing potassium as counter cation.

Naturally occurring or synthetically produced zeolites may contain more than one metal counter cation in the structure. Thus for example, calcium chabazite may contain a small amount of potassium ions (e.g. 1.0 wt % based on the weight of the zeolite) in addition to the predominant calcium counter cations (2.8 wt % based on the weight of the zeolite). Such zeolites which contain small amounts of potassium (wt % based on the weight of the zeolite) relative to the predominant counter cation are not within the scope of the present invention which employs zeolites which have potassium as the predominant counter cation (wt % based on the weight of the zeolite).

The preferred zeolites may be potassium cation-exchanged forms of common zeolites, the potassium cation-exchanged form having a mean pore size in the range between 3.5 Å and 4.8 Å, that is they are zeolites which have been produced by potassium cation-exchange with commercially available starting zeolites. The starting zeolite may be, for example, a an erionite, or it may be a mixture of zeolites containing erionite, for example a mixture of chabazite and erionite or a mixture of offrotite and erionite. A preferred starting zeolite is a calcium chabazite/erionite mixture, commercially available as AW-500. Surprisingly, we have found that the exchange of potassium ions for calcium ions in AW-500 leads to a substantial reduction in the effective size of the pores of the zeolite, resulting in a substantial increase in the selectivity of the erionite portion of the zeolite for the adsorbtion of HCFC 1122.

The process of ion exchange to produce the ion-exchanged form of zeolite is a conventional technique, described for example in The Journal of Physical Chemistry, 66, 812–16 (1962). Typically, the starting zeolite, for example AW-500 may be immersed in a dilute aqueous solution of a potassium salt. The anion of the potassium salt is generally irrelevant for the purposes of the present invention but is preferably a halide, and particularly a chloride, for example, KCl so that the salt is water soluble. The solution containing the zeolite may be stirred for an appropriate period of time, for example from about a few hours, say 2–3 hours, to about a few days, say 2–3 days, at about room or elevated temperature and the liquid then decanted. This process may be repeated several times to ensure a high degree of exchange and the zeolite may then be washed with water and dried.

The degree of cation-exchange, that is the % of the original predominant counter cation in the starting zeolite which is replaced by potassium, for example, the % of $Ca^{++}$ ions replaced in starting zeolite AW-500, may be controlled at least to some extent by varying the time for which the starting zeolite is immersed in the potassium salt solution. The degree of cation-exchange may be varied within a wide range depending upon, inter alia, the starting zeolite, it being generally observed that as the degree of cation-exchange increases, so the selectivity of the cation-exchanged form of the zeolite for HCFC 1122 increases. Where the starting zeolite is zeolite AW-500, it is preferred, for optimum results, that the degree of cation-exchange is at least 30%, more preferably at least 50%. However, the degree of cation-exchange may be significantly less than the above ranges, provided that the degree of cation-exchange is sufficient as to produce a potassium cation-exchanged zeolite in which potassium is the predominant counter cation, whilst still providing improved adsorption selectivity for HCFC 1122.

Prior to use of the potassium-exchanged zeolite in the process of the invention, the zeolite should be dried and this may be achieved, for example, by heating the zeolite to a temperature of between about 200° C. and about 400° C. in a nitrogen atmosphere at atmospheric pressure or at a lower temperature under sub-atmospheric pressure.

In the process of the invention, HFA 134a containing HCFC 1122 and optionally other hydrofluorocarbons may be contacted with the cation-exchanged form of zeolite by passing a stream of HFA 134a in the liquid or vapour phase over a bed of zeolite particles. The bed may be a fixed bed. Alternatively various other techniques, known in the art, may be used for contacting an HFA 134a stream with the zeolite adsorbent, such as for example, contacting the stream with a fluidised or moving bed of adsorbent zeolite particles. Selection of the particle size and bed shape may be varied within a broad range and may be determined according to known principles. The zeolite particle size depends at least to some extent upon whether vapour phase or liquid phase contacting is employed and upon the scale of the process, but overall the particle size will usually be in the range from about 1 micrometer to about 5 centimeters, and preferably from about 50 micrometers to about 1 centimeter.

The hourly space velocity of the HFA 134a stream over the zeolite may be varied within a wide range. Generally, HFA 134a vapour may be passed over the zeolite with a gas hourly space velocity of 130 to 3600 $hr^{-1}$, although the gas hourly space velocity may be much greater than this if desired, particularly at lower temperatures. The corresponding liquid hourly space velocity for liquid phase operation is 1 to 30 $hr^{-1}$.

The temperature at which the purification process is carried out will typically be in the range from about −30° C. to about 100° C. The pressure at which the process is carried out may be dependent to some extent upon whether liquid or vapour phase contacting is desired but will usually be in the range from about 1.0 to about 40 bar.

Typically, the HFA 134a as produced by conventional processes, and treated by the process of the invention will contain from about 10 to about 10000 ppm HCFC 1122 although it may contain a substantially higher concentration of HCFC 1122. Use of potassium-exchanged zeolites allows the removal of HCFC 1122 from HFA 134a to a very low level, generally below 5 ppm, and even below 2 ppm, depending to some extent on the initial HCFC 1122 content of the HFA 134a.

HFA 134a as produced by known processes may contain further contaminants in addition to HCFC 1122. These contaminants include, for example, single-carbon and two-carbon species containing hydrogen, chlorine and fluorine, as well as unreacted hydrogen fluoride and by-product hydrogen chloride (which is a major by-product from most known HFA 134a production processes). The hydrogen fluoride and hydrogen chloride can be removed by known techniques; preferably, since hydrogen fluoride and hydrogen chloride may attack the zeolites used in the process of the invention, the removal of hydrogen fluoride and hydrogen chloride is carried out prior to contacting the HFA 134a stream with the zeolite. Other contaminants are typically present in only very small amounts and many may be removed by distillation.

Whilst many of the zeolites hitherto known for removing HCFC 1122 from HFA 134a may have also adsorbed at least some of these minor contaminants, thus reducing the selectivity of these zeolites for adsorbing HCFC 1122, the zeolites of the present invention have little capacity for adsorption of these minor contaminants and adsorption of HCFC 1122 is therefore highly selective with respect to these contaminants.

The adsorbent zeolite bed will require regeneration or reactivation when its capacity for adsorbing HCFC 1122 has been filled. Regeneration may be, for example, by heating the bed in a gas stream, usually nitrogen or air, to desorb the HCFC 1122. However, the frequency with which the bed must be regenerated may be significantly reduced when compared with a bed of the zeolites used heretofore. After the bed has been heated and HCFC 1122 fully removed or even partially removed from it, it may be cooled and re-introduced into service. The conditions required for optimal regeneration of the adsorbent will be determined by the particular adsorbent used and the available utilities and are readily determined by simple routine experiment. Typically, heating the bed of adsorbent to between about 70° C. and about 400° C. within a stream of nitrogen gas or air provides satisfactory regeneration.

The invention is illustrated by the following examples.

EXAMPLE 1

Preparation of Potassium Ion-Exchanged Form of Zeolite AW-500

100 g of AW-500 (supplied by UOP) having an extrudate size of 1.6 millimeters was immersed in a solution of potassium chloride (17 g) in water (1500 ml) and the mixture was stirred at 50° C. for 6 hours. At the end of this time the mixture was allowed to settle and the liquid was decanted. The procedure was repeated 3 times with the same sample. The solid product was then washed with de-ionised water, and dried for several hours in a stream of nitrogen at 200° C. until there was no further measurable loss of weight.

The potassium exchanged sample was then analysed to determine its potassium and calcium contents, and hence the extent of ion-exchange achieved. Potassium and calcium were determined as in the weight ratio K 7.6:Ca 0.8, whereas in the starting AW-500 the calcium and potassium contents were K 1.0:Ca 2.75. The calcium ions are replaced by potassium ions so that the proportion of calcium originally present which had been replaced by potassium was (2.75–0.8)/2.75 or 70%.

Removal of HCFC 1122 from HFA 134a

The procedure described below was carried out with the potassium ion-exchanged AW-500 from example 1 and also with untreated AW-500 (supplied by UOP and containing calcium cations) for comparison purposes. 6 g of the zeolite to be tested was packed into a reactor tube to give a zeolite bed of 7.5 mls.

Liquid HFA 134a containing 200 ppm HCFC 1122 was fed through a vaporiser and then through the zeolite bed at a vapour flow rate of 200 mls/minute. The concentration of HCFC 1122 in the exit gas was determined by gas chromatography and the results are shown in graphic form in FIG. 1, in which "bed residences" is the volume of the 134a/1122 mixture passed over the zeolite bed divided by the volume of the zeolite bed.

Figure 1:
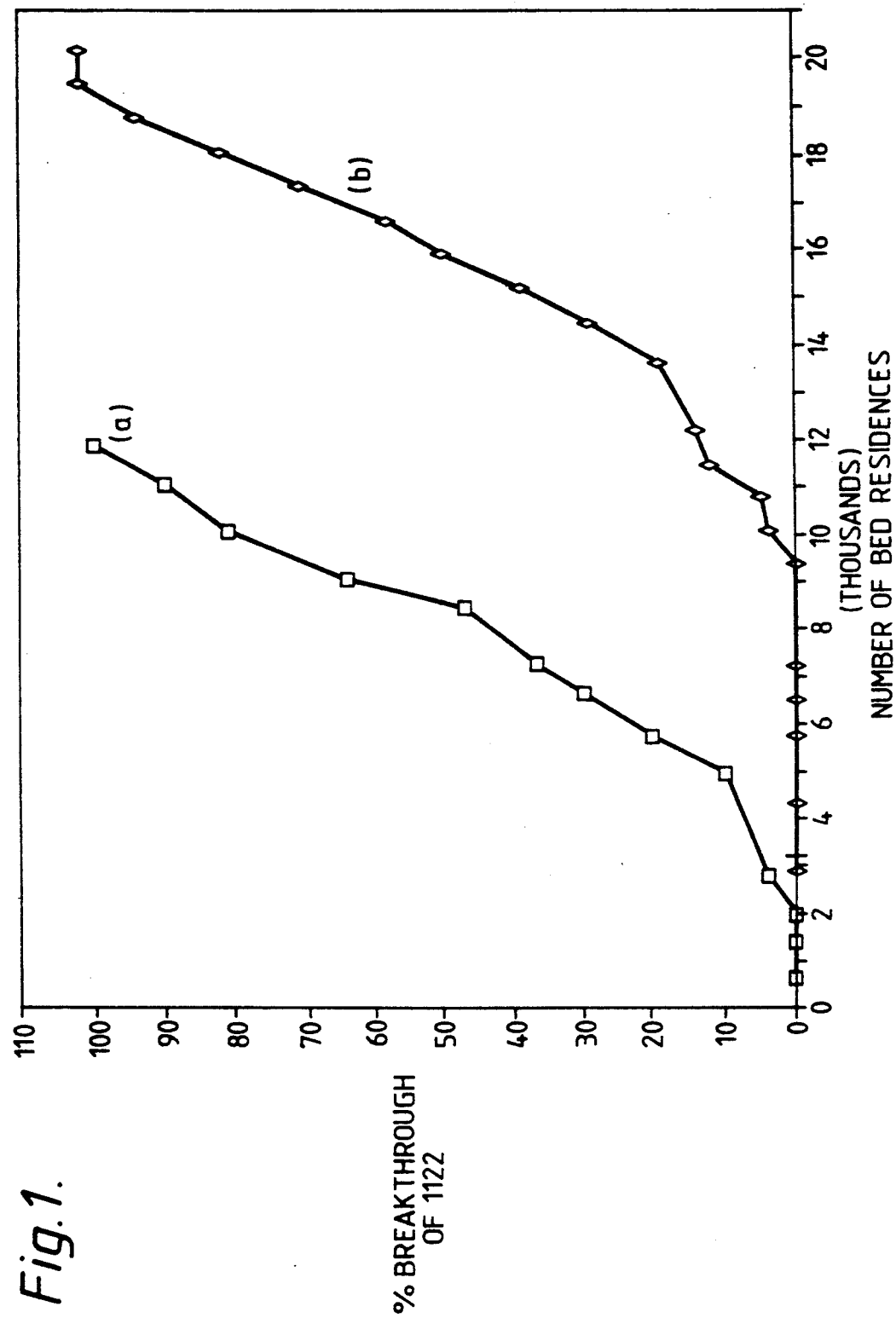
In FIG. 1, line (a) is the vapour breakthrough curve for the untreated AW-500 zeolite whilst line (b) is the vapour breakthrough curve for the potassium ion-exchanged form of AW-500 produced in example 1.

The results show that HCFC 1122 begins to appear in the exit gas after far less HFA 134a/HCFC 1122 mixture has been passed over the zeolite bed when the zeolite is untreated AW-500 than when the zeolite is the potassium-ion exchanged form of AW-500 produced in example 1. The results thus show that the selectivity of the potassium ion-exchanged form of AW-500 for removing HCFC 1122 from the stream of HFA 134a/1122 mixture is substantially greater than the selectivity of untreated AW-500.

EXAMPLE 2

A 100 ml aerosol container was charged with 1.95 g of the potassium ion-exchanged form of AW-500 produced in example 1 and 46.1 g of liquid HFA 134a containing 152 ppm HCFC 1122. The aerosol was sealed and allowed to stand for 24 hours at ambient temperature after which time the liquid was analysed by gas chromatography. The level of HCFC 1122 in the liquid had been reduced to 2.2 ppm.

EXAMPLE 3

The procedure of example 2 was repeated except that the aerosol container was charged with 1.6 g of the potassium ion-exchanged form of AW-500 produced in example 1 and 51 g of liquid HFA 134a containing 152 ppm HCFC 1122. After 24 hours the level of HCFC 1122 in the liquid had been reduced to 5 ppm.

COMPARATIVE EXAMPLE 1

The procedure of example 2 was repeated except that the aerosol container was charged with 4.0 g of the untreated AW-500 and 49 g of liquid HFA 134a containing 152 ppm HCFC 1122. After 24 hours the level of HCFC 1122 in the 134a phase had been reduced to 5 ppm.

COMPARATIVE EXAMPLE 2

The procedure of example 2 was repeated except that the aerosol container was charged with 4 g of zeolite 3A and 40 g of liquid HFA 134a containing 39.3 ppm HCFC 122. After 24 hours the level of HCFC 1122 in the 134a phase remained 39.3 ppm. Zeolite 3A is a zeolite containing potassium ions as predominant counter cations and having a mean pore size of 3.0 Å.

We claim:

1. A process for the removal of 1-chloro-2,2-difluoroethylene from 1,1,1,2-tetrafluoroethane which comprises contacting 1,1,1,2-tetrafluoroethane containing 1-chloro-2,2-difluoroethylene with a zeolite having a mean pore size in the range of 3.5 Å to 4.8 Å and having potassium as the predominant counter cation.

2. A process as claimed in claim 1 in which the zeolite has a mean pore size in the range from about 3.5 Å to about 4.5 Å.

3. A process as claimed in claim 1 in which the zeolite has a mean pore size in the range from about 3.6 Å to about 4.2 Å.

4. A process for the removal of 1-chloro-2,2-difluoroethylene from 1,1,1,2-tetrafluoroethane by contacting 1,1,1,2-tetrafluoroethane containing 1-chloro-2,2-difluoroethylene with a zeolite having a mean pore size in the range of about 3.5 Å to about 4.8 Å and having potassium as a counter cation wherein the zeolite is produced by potassium-cation exchange with a starting zeolite comprising at least one of errionite, offrotite and chabazite.

5. A process as claimed in claim 4 in which the starting zeolite comprises AW-500 zeolite.

6. A process as claimed in claim 4 in which the degree of cation-exchange is at least 30%.

7. A process as claimed in claim 4 in which the degree of cation-exchange is at least 50%.

8. A process as claimed in claim 1 in which the 1,1,1,2-tetrafluoroethane containing 1-chloro-2,2-difluoroethylene in the liquid or vapour phase is passed over a bed of zeolite particles.

9. A process as claimed in claim 1 in which the temperature is in the range from about −30° C. to about 100° C.

10. A process as claimed in claim 1 wherein the 1,1,1,2-tetrafluoroethane to be contacted with the zeolite contains from about 10 to about 10000 ppm of 1-chloro-2,2-difluoroethylene and whereby 1,1,1,2-tetrafluoroethane containing less than 5 ppm of 1-chloro-2,2-difluoroethylene is recovered.

* * * * *